United States Patent [19]

Khademazad et al.

[11] Patent Number: 5,803,730
[45] Date of Patent: Sep. 8, 1998

[54] MOBILOMETER

[76] Inventors: Behrooz Khademazad, 1524 Tuley St., Cedar Hill, Tex. 75104; Kamrooz Khademazad, Private Mail Bag/University of Technology, Department of Electrical Engineering, Lae, Papua, New Guinea; Courosh Mehanian, 160 Rio Robles, San Joe, Calif. 95134

[21] Appl. No.: 616,691

[22] Filed: Mar. 15, 1996

[51] Int. Cl.[6] .................................................. A61C 19/04
[52] U.S. Cl. ............................ 433/72; 128/776; 356/373; 433/215
[58] Field of Search ...................... 433/72, 215; 128/776, 128/777; 33/513, 514; 250/221, 222.1; 356/373

[56] References Cited

U.S. PATENT DOCUMENTS

| | | |
|---|---|---|
| 285,977 | 10/1883 | Dennis . |
| 3,943,913 | 3/1976 | Johnson . |
| 4,192,321 | 3/1980 | Korber et al. ........................... 128/776 |
| 4,470,810 | 9/1984 | Bourdeau et al. ...................... 433/215 |
| 4,499,906 | 2/1985 | Wohlgemuth et al. ................. 128/776 |
| 4,881,552 | 11/1989 | Heyman .................................. 128/776 |
| 4,979,898 | 12/1990 | Rawd ....................................... 433/72 |

FOREIGN PATENT DOCUMENTS

| | | |
|---|---|---|
| 243640 | 3/1987 | German Dem. Rep. ................. 433/72 |
| 2162683 | 6/1973 | Germany . |
| 3127731 | 2/1983 | Germany ................................. 433/72 |
| 4003947 | 8/1991 | Germany ................................. 128/777 |
| 1212421 | 2/1986 | U.S.S.R. ................................... 433/72 |
| 1648444 | 5/1991 | U.S.S.R. ................................... 433/72 |

OTHER PUBLICATIONS

Smith et al, *Instrument for Measuring Tooth Mobility*, Rev. Sci. Instrum 50(12) pp. 1645–1648, Dec. 1979.

*Primary Examiner*—Ralph Lewis
*Attorney, Agent, or Firm*—Sidley & Austin

[57] ABSTRACT

Measuring apparatus and method for measuring the mobility of an object, such as a tooth, having a longitudinal axis, that is disposed in a securing medium. The apparatus includes an outer and an inner housing. The outer housing partially defines a cavity and has first and second cavity wall portions which face the cavity and position the outer housing with respect to the securing medium. The inner housing is disposed within the cavity and partially defines a chamber that receives the object. The inner housing is adapted for relative movement with respect to the outer housing. The inner housing has first and second chamber wall portions facing the chamber and first and second object contact members for engaging opposing surfaces of the object. First and second compression springs are positioned between and in contact with respective chamber wall portions and object contact members. When pressed a force transmitting member connected to the inner housing causes the inner housing to move radial to the longitudinal axis of the object. Optic fibers fixed to the outer housing and connected to a detector measure the mobility of the object with respect to the securing medium by receiving a beam of light emitted from a directional light source fixed to one of the object contact members.

21 Claims, 3 Drawing Sheets

MOBILOMETER

FIELD OF THE INVENTION

The present invention generally relates to a method and an apparatus for measuring the mobility of an object. In a specific aspect, the present invention relates to a method and an apparatus for measuring the mobility of a tooth.

BACKGROUND OF THE INVENTION

Throughout history there has been a need to measure the mobility of objects which are partially within and at least loosely secured by a securing medium. The mobility of these objects is commonly measured by exerting a known force on an object and measuring any resulting movement of the object with respect to the securing medium. Traditional devices have been developed in an attempt to satisfy this need. However, these devices are not sufficiently applicable to many different specific applications such as the measuring of the mobility of a tooth, the measuring of movements of the nasal septum during rhinoplasty surgery, the measuring of the mobility of dental and other types of implants in different areas of the body, and the measuring of valve stems and other movable parts needing to be measured. Thus, there is a need in the art for an apparatus that allows for the measurement of the mobility of objects in many different specific applications.

One application of traditional apparatuses has been in the area of dentistry. In dentistry, tooth mobility signifies the degree of looseness of a tooth which provides an indication of the extent of periodontal disease or deterioration of the securing medium of the tooth, namely the attached gingiva and alveolar bone. Thus, when examining the condition of teeth, it is often useful to determine the mobility of an individual tooth in response to an applied force.

Accordingly, tooth mobility measuring apparatuses have been devised to apply increasing pressure on a tooth and to measure its resulting relative displacement with respect to adjacent teeth. These traditional tooth mobility measuring apparatuses include those disclosed in U.S. Pat. No. 4,192,321, U.S. Pat. No. 3,943,913, and German Offenlegungsschrift 21 62 683. However, these traditional tooth mobility measuring apparatuses provide only limited use of a tooth mobility measuring apparatus in a clinical setting. Moreover, analysis of tooth mobility data collected by such apparatuses is too expensive, time consuming, and impractical in a clinical setting. Thus, traditional tooth mobility measuring apparatuses have not provided feasible means to effectively obtain accurate and precise information in a dental office.

In addition, these traditional tooth mobility measuring apparatuses require placement of the apparatus on several teeth at one time in order for any measurement to be taken. Thus, these traditional tooth mobility measuring apparatuses do not allow for all instances found inside a patient's mouth (e.g., where the measured tooth is not surrounded by two adjacent teeth). The traditional tooth mobility measuring apparatuses are also bulky and difficult to position within a patient's mouth. Thus, there is also a need for a practical, universally usable and accurate apparatus for measuring the mobility of a tooth.

SUMMARY OF THE INVENTION

The apparatus and method of the present invention overcome many of the disadvantages found in the prior art by serving to objectively and accurately measure the mobility of an object.

An apparatus in accordance with the present invention for measuring the mobility of an object, such as a tooth, having a longitudinal axis, a portion of the object being within and at least loosely secured by a securing medium, includes an outer housing and an inner housing. The outer housing at least partially defines a cavity. The outer housing has a first cavity wall portion and a second cavity wall portion which face the cavity, and are adapted to position the outer housing with respect to the securing medium when the object is disposed within the cavity. The inner housing is disposed within the cavity that is at least partially defined by the outer housing. The inner housing at least partially defines a chamber capable of receiving the object. The inner housing has a first chamber wall portion facing the chamber and a second chamber wall portion facing the chamber. The first and second chamber wall portions extend along lines which are generally in the same direction as the longitudinal axis of the object when the object is disposed within the chamber. The inner housing is adapted for relative movement with respect to the outer housing along a radius to the longitudinal axis of the object. The apparatus also includes first and second object contact members for contacting the object. A first compression spring is positioned between and in contact with the first chamber wall portion and the first object contact member. A second compression spring is positioned between and in contact with the second chamber wall portion and the second object contact member. The first and second object contact members engage opposing sides of the object when the object is disposed within the chamber. The first inner cavity wall portion has an opening therethrough through which a force transmitting member extends so that when the force transmitting member is pressed, the inner housing is moved relative to the outer housing in a direction that is generally radial to the longitudinal axis of the object. A directional light source for emitting a beam of light generally parallel to the longitudinal axis of the object is fixed to one of the object contact members. A plurality of optic fibers is fixed to the outer housing so as to receive a beam of light emitted from the directional light source. The plurality of optic fibers are in communication with a detector for ascertaining which of the optic fibers receives light emitted from the directional light source when the apparatus is disposed about the object, the force transmitting member is pressed and the object moves in a direction that is generally radial to the longitudinal axis of the object. The detector provides an output indicative of the amount of mobility of the object with respect to the securing medium.

A method in accordance with the present invention for measuring the mobility of an object, such as a tooth, includes the steps of: positioning an apparatus about the object; abutting an object contact member against the object; pressing a force transmitting member so as to cause the object contact member to exert a force onto the object; moving the object in a direction radial to the longitudinal axis of the object; and, calculating the mobility of the object with respect to the securing medium.

The apparatus of the present invention can be generally referred to as a mobilometer. In a specific application, the apparatus of the present invention can be referred to as a dentomobilometer.

The apparatus of the present invention can be used in many different specific applications including the measuring of movements of the nasal septum during rhinoplasty surgery, the measuring of mobility of dental and other types of implants in different areas of the body, and the measuring of valve stems and other movable parts needing to be measured. The present invention can also be used with minor alterations in other trades such as carpentry, plumbing, electrical, chemical engineering, architectural, electrical engineering, structural engineering, nuclear physics and other sciences. Moreover, the present invention provides an apparatus that is easy to use. Thus, the present invention provides a practical, universally usable and accurate apparatus.

In a specific aspect, the apparatus of the present invention satisfies the need in the art for standardizing the movement of teeth and odontogenic structures for the purpose of diagnosing periodontal disease. The present invention is an apparatus that can be used on all teeth. This apparatus is small enough to fit over a single tooth and to be maneuvered around comfortably inside a patient's mouth. This apparatus standardizes the measurement of tooth mobility for the dental profession so as to improve diagnosis and prognosis of teeth before and after treatment.

DETAILED DESCRIPTION OF THE INVENTION

Figure 1:
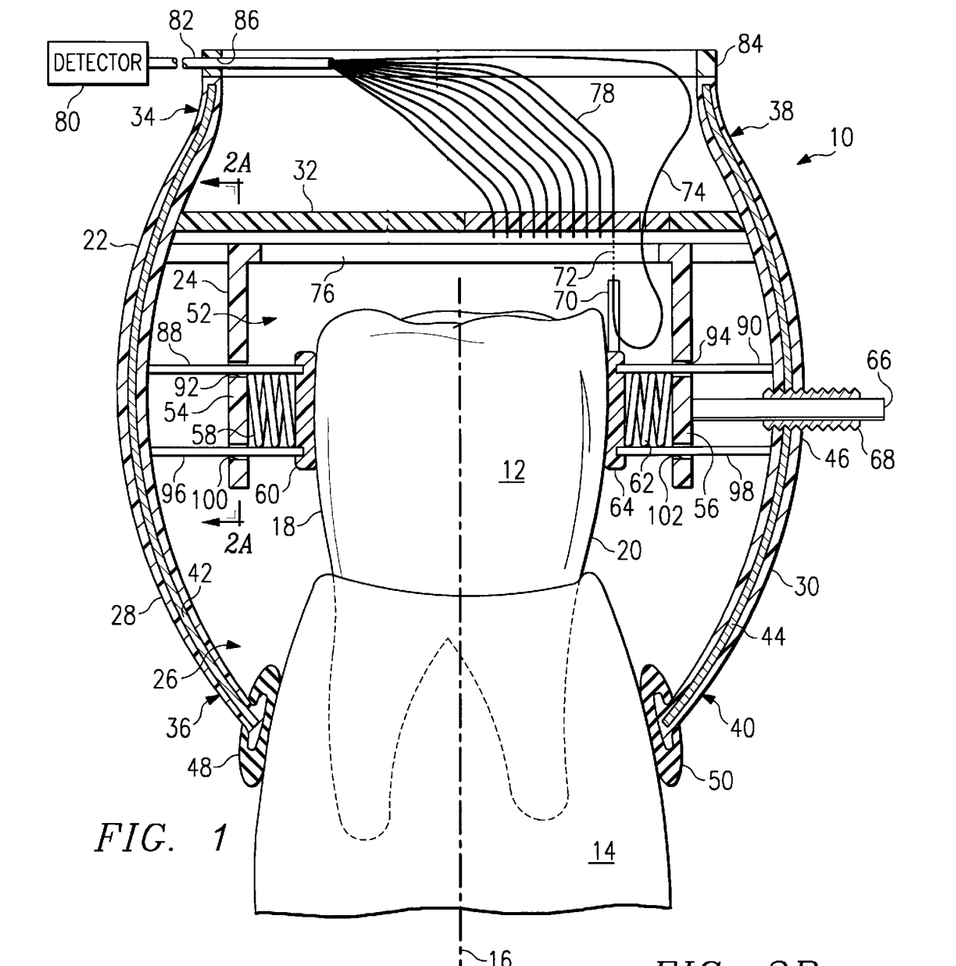
FIG. 1 depicts a generally vertical cross sectional view of an apparatus positioned about a tooth in accordance with the present invention.

FIG. 1 illustrates an apparatus 10 in accordance with the present invention for measuring the mobility of an object 12 with respect to a securing medium 14. A portion of the object 12 is within and at least loosely secured by the securing medium 14. The object 12 has a longitudinal axis 16 and opposing sides 18 and 20. Unless otherwise stated, radial directions are directions which are radial to the longitudinal axis 16 of the object 12, and axial directions are directions which are parallel to the longitudinal axis 16 of the object 12.

The apparatus 10 includes an outer housing 22 and an inner housing 24. The outer housing 22 at least partially defines a cavity 26. The outer housing 22 includes a cavity wall portion 28 and a cavity wall portion 30 which extend along lines which are generally in the same direction as the longitudinal axis 16 when the apparatus 10 is positioned about the object 12. The cavity wall portions 28 and 30 face the cavity 26. The cavity wall portions are pivotally connected to a connecting member 32. The cavity wall portion 28 includes an upper portion 34 that extends above the connecting member 32 and a lower portion 36 that extends below the connecting member 32. The cavity wall portion 30 includes an upper portion 38 that extends above the connecting member 32 and a lower portion 40 that extends below the connecting member 32. The cavity wall portions 28 and 30 are adapted to position the outer housing 22 with respect to the securing medium 14 when the object 12 is disposed in the cavity 26.

By exerting a force that is external to the apparatus 10 and that is in a direction that is radial to the longitudinal axis 16 of the object 12 onto the upper portion 34 of the cavity wall portion 28, the cavity wall portion 28 can pivot with respect to the connecting member 32 such that the lower portion 36 of the cavity wall portion 28 can be removed from engagement with the securing medium 14. Moreover, by releasing such a force and by positioning the apparatus 10 about the object 12, the lower portion 36 of the cavity wall portion 28 can engage the securing medium 14.

Likewise, by exerting a force that is external to the apparatus 10 and that is in a direction that is radial to the longitudinal axis 16 of the object 12 onto the upper portion 38 of the cavity wall portion 30, the cavity wall portion 30 can pivot with respect to the connecting member 32 such that the lower portion 40 of the cavity wall portion 30 can be removed from engagement with the securing medium 14. Moreover, by releasing such a force and by positioning the apparatus 10 about the object 12, the lower portion 40 of the cavity wall portion 30 can engage the securing medium 14.

Thus, the cavity wall portions 28 and 30 provide a primary source of stability to the apparatus 10. To afford additional stability to the cavity wall portions 28 and 30, the outer housing 22 can include rigid members 42 and 44. The rigid member 42 can be contained within or can be secured to the cavity wall portion 28 of the outer housing 22 such that the cavity wall portion 28 is not prevented from pivoting with respect to the connecting member 32. Likewise, the rigid member 44 can be contained within or can be secured to the cavity wall portion 30 of the outer housing 22 such that the cavity wall portion 30 is not prevented from pivoting with respect to the connecting member 32.

The cavity wall portion 30 includes an opening 46 which extends through the cavity wall portion 30 in a direction which is at least generally radial to the longitudinal axis 16.

The cavity wall portion 28 can include a securing medium contact member 48 for contacting one side of the securing medium 14. The cavity wall portion 30 can include a securing medium contact member 50 for contacting an opposing side of the securing medium 14.

The inner housing 24 is disposed within the cavity 26. The inner housing 24 at least partially defines a chamber 52 which is capable of receiving the object 12. The inner housing 24 includes a chamber wall portion 54 and a chamber wall portion 56. The chamber wall portions 54 and 56 face the chamber 52. The chamber wall portions 54 and 56 extend along lines which are generally in the same direction as the longitudinal axis 16 of the object 12 when the object 12 is disposed within the chamber 52.

The inner housing 24 is adapted for relative movement with respect to the outer housing 22. As a result, the inner housing 24 can move with respect to the outer housing 22 in a direction that is radial to the longitudinal axis 16 of the object 12.

A compression spring 58 is positioned between and in contact with the chamber wall portion 54 and an object contact member 60. A compression spring 62 is positioned between and in contact with the chamber wall portion 56 and an object contact member 64. Thus, the object contact members 60 and 64 can engage the opposing sides 18 and 20 of the object 12 when the object 12 is disposed with the chamber 52. The spring force constant of the compression spring 58 is at least about as the spring force constant of the compression spring 62. Thus, when the apparatus 10 is disposed about the object 12 in its initial position as shown in FIG. 1, the forces that the object contact members 60 and 64 exert on the object 12 are about equal and are oppositely disposed. Preferably, when the apparatus 10 is disposed about the object 12 as shown in FIG. 1, the forces exerted by the object contact members 60 and 64 cancel each other so that they do not exert a net force on the object 12.

A force transmitting member 66 is provided to exert a net force on the object 12 to measure the mobility of the object 12 with respect to the securing medium 14. The force transmitting member 66 extends through the opening 46 in the cavity wall portion 30 of the outer housing 22. By pressing the force transmitting member 66, the inner housing 24 is moved in a direction that is generally radial to the longitudinal axis 16 of the object 12. The resulting movement of the inner housing 24 compresses the compression spring 62 and partially relaxes the compression spring 58. As a result, the object contact member 64 exerts a force onto the object 12.

The amount of force that is exerted on the object 12 as a result of pressing the force transmitting member 66 can be altered by use of a threaded member 68. The threaded member 68 can adjustably mate with a correspondingly threaded opening 46 in the cavity wall portion 30 of the outer housing 22. By adjusting the relative position of the threaded member 68 with respect to the cavity wall portion 30, the amount of depression of the force transmitting member 66 can be altered which correspondingly alters the amount of force exerted on the object 12.

As a force is exerted on the object 12, the object 12 may move in a direction that is radial to the longitudinal axis 16. As the object 12 moves in this direction, the object contact members 60 and 64 are maintained in engagement with the object 12 by the compression springs 58 and 62. Thus, the object contact members 60 and 64 are also moving in a directional that is radial to the longitudinal axis 16 to the same extent that the object 12 is moving with respect to the securing medium 14. Correspondingly, the object contact members 60 and 64 are moving relative to the outer housing 22 which is fixed with respect to the securing medium 14. As a result, the mobility of the object 12 with respect to the securing medium 14 can be measured by measuring any relative movement of the object contact members 60 and 64 with respect to the outer housing 22. Thus, in order to measure the mobility of the object 12 in response to an applied force, a directional light source 70 can be placed on either of the object contact members 60 and 64. As shown in FIG. 1, the directional light source 70 is disposed on the object contact member 64.

The directional light source 70 can emit a beam of light 72. Preferably, the directional light source 70 emits the beam of light 72 in a direction that is generally parallel to the longitudinal axis 16 of the object 12. The directional light source 70 can be supplied with light by a light supply fiber 74. As the directional light source 70 emits the beam of light 72, the beam of light 72 is emitted through an opening 76 in the inner housing 24 and is directed toward a plurality of optic fibers 78. The plurality of optic fibers 78 are secured to the connecting member 32 so that at least one of the optic fibers 78 can receive the beam of light 72. The plurality of optic fibers 78 are in communication with a detector 80 which serves to ascertain which of the optic fibers 78 receive the light beam 72 as a result of any movement of the object 12 in a direction that is radial to the longitudinal axis 16. The detector 80 provides an output which is indicative of the amount of mobility of the object 12 with respect to the securing medium 14. The optic fibers 78 can be connected to the detector 80 via piezoelectric sensor technology. The detector 80 can be a digital micrometer.

The plurality of optic fibers 78 can be gathered to exit the apparatus 10 through a tube 82. The position of the tube 82 with respect to the apparatus 10 can be altered by the inclusion of a rotatable member 84 that is rotatably secured to the outer housing 22. The rotatable member 84 includes an opening 86 therethrough through which the tube 82 and/or the plurality of optic fibers 78 can extend. Thus, by rotating the rotatable member 84 with respect to the apparatus 10, the relative position of the optic fibers 78 with respect to the apparatus 10 can be altered.

In order to engage and remove the object contact members 60 and 64 with respect to the object 12, the apparatus 10 can also include a tension wire 88 and a tension wire 90. One end of the tension wire 88 is connected to the cavity wall portion 28 of the outer housing 22 and the other end is connected to the object contact member 60. The tension wire 88 extends from the cavity wall portion 28 through an opening 92 in the chamber wall portion 54 of the inner housing 24 to the object contact member 60. One end of the tension wire 90 is connected to the cavity wall portion 30 and the other end is connected to the object contact member 64. The tension wire 90 extends from the cavity wall portion 30 through an opening 94 in the chamber wall portion 56 of the inner housing 24 to the object contact member 64. As shown in FIG. 1, tension wires 96 and 98 can also be included. One end of the tension wire 96 is connected to the cavity wall portion 28 and the other end is connected to the object contact member 60. The tension wire 96 extends from the cavity wall portion 30 through an opening 100 in the chamber wall portion 54 of the inner housing 24 to the object contact member 60. One end of the tension wire 98 is connected to the cavity wall portion 30 and the other end is connected to the object contact member 64. The tension wire 98 extends from the cavity wall portion 30 of the outer housing 22 through an opening 102 in the chamber wall portion 56 of the inner housing 24 to the object contact member 64.

As mentioned above, the position of the cavity wall portions 28 and 30 can be altered with respect to the securing medium 14. This movement of the lower portions of the cavity wall portions 28 and 30 away from the securing medium 14 serves to exert a tension on the tension wires 88, 90, 96 and 98. As a result, the tension wires 88 and 96 can serve to retract the object contact member 60 from engagement with the object 12 and the tension wires 90 and 98 can serve to retract the object contact member 64 from engagement with the object 12. Correspondingly, by releasing a compressive force applied to the upper portion 34 of the cavity wall portion 28 and a compressive force applied to the upper portion 38 of the cavity wall portion 30, the lower portion 36 of the cavity wall portion 28 and the lower portion 40 of the cavity wall portion 30 move toward each other and release tension in the tension wires 88, 90, 96 and 98 such that the compression spring 58 serves to contact the object contact member 60 to the side 18 of the object 12 and the compression spring 62 serves to contact the object contact member 64 to the side 20 of the object 12. Thus, the apparatus 10 can be conveniently positioned about the object 12 so as to measure the mobility of the object 12 and then be readily removed from about the object 12.

Figure 2A:
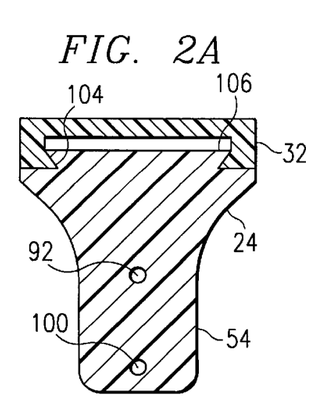
FIG. 2A depicts a cross sectional view of a portion of the apparatus depicted in FIG. 1, taken along the line 2A—2A in FIG. 1.

FIG. 2A, wherein the same reference characters are utilized for parts which are in common with FIG. 1, depicts a cross sectional view of the connecting member 32 and the chamber wall 54 of the inner housing 24, taken along the line 2A—2A in FIG. 1. FIG. 2A depicts a design of the inner housing 24 and of the outer housing 22 that allows for movement of the inner housing 24 with respect to the outer housing 22. The connecting member 32 of the outer housing 22 is provided with a dovetail slot 104 in its lower surface which extends radially with respect to the longitudinal axis 16. The upper portion of the inner housing 24 has a dovetail configuration 106 which slidably and securely fits within the dovetail slot 104 for relative motion between the inner housing 24 and the outer housing 22. The openings 92 and 100 for the tension wires can also be seen in FIG. 2A.

Figure 2B:
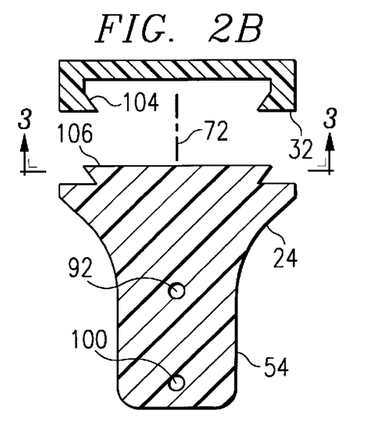
FIG. 2B depicts an exploded view of FIG. 2A.

FIG. 2B depicts an exploded view of FIG. 2A and further depicts the beam of light 72 exiting the inner housing 24 and entering the outer housing 22. A bearing medium (not shown) can be included between the inner housing 24 and the outer housing 22 to provide a low friction surface therebetween.

Figure 3:
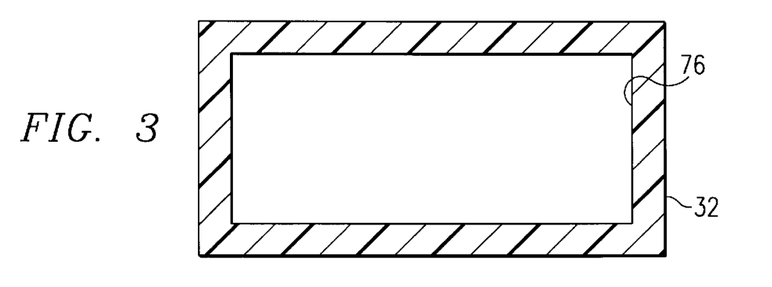
FIG. 3 depicts a cross sectional view of a portion of the portion of the apparatus depicted in FIG. 2B, taken along the line 3—3 in FIG. 2B.

FIG. 3 depicts a cross sectional view of a portion of the outer housing 22 of the apparatus 10 depicted in FIG. 2B taken along the line 3—3 in FIG. 2B. The opening 76 in the connecting member 32 of the outer housing 22 allows the light beam 72 to be emitted therethrough.

Figure 4:
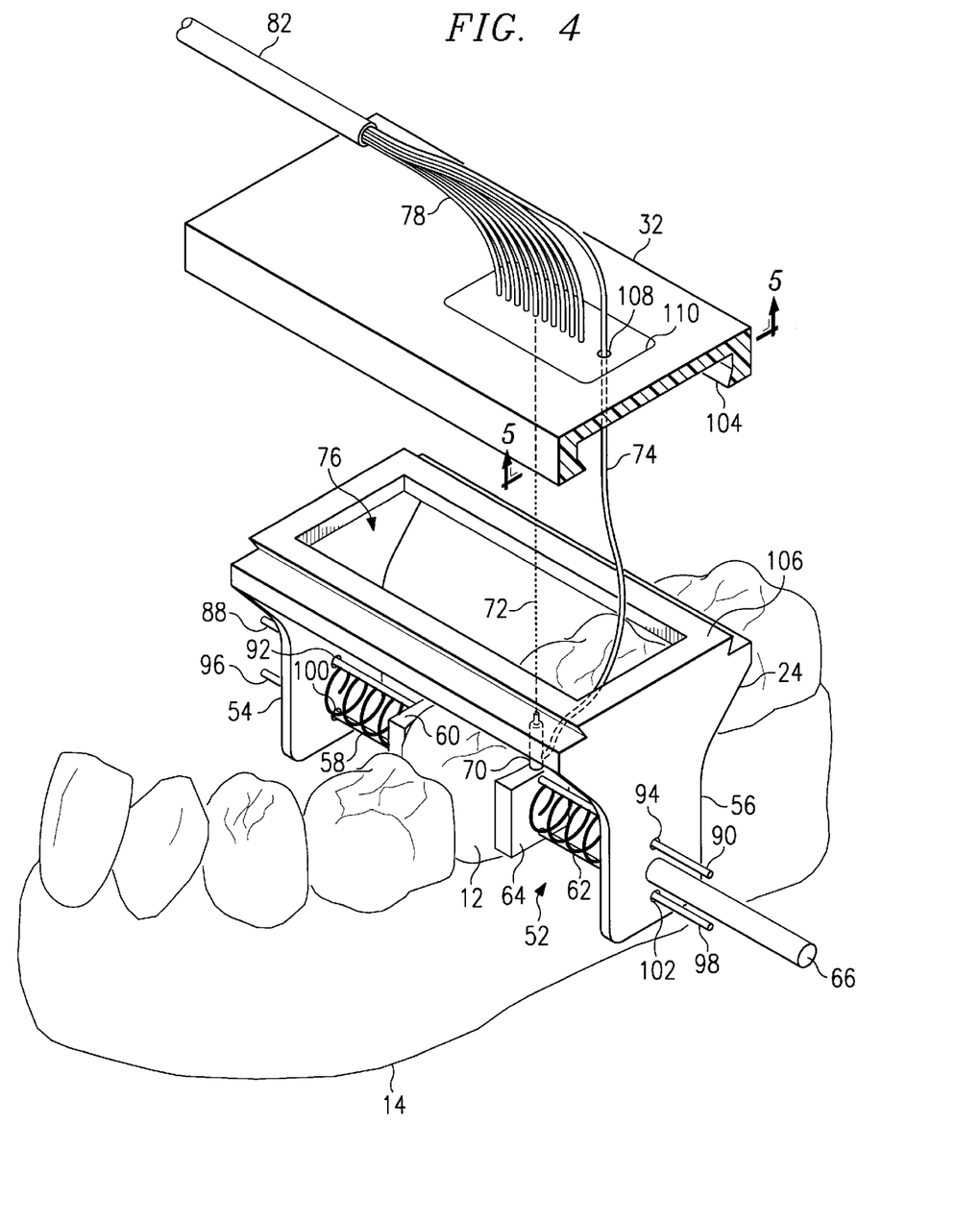
FIG. 4 depicts an exploded view of a portion of the apparatus of FIG. 1.

FIG. 4, wherein the same reference characters are utilized for parts which are in common with FIG. 1, depicts an exploded view of a portion of the apparatus 10 depicted in FIG. 1. FIG. 4 depicts a portion of the outer housing 22 and the inner housing 24 which more clearly depicts the emission of the light beam 72 through the opening 76 in the outer housing 22. The light supply fiber 74 extends from the directional light source 70 through the opening 76 in the inner housing 24 and through an opening 108 in the outer housing 22. The plurality of optic fibers 78 are secured to the connecting member 32 of the outer housing 22 and can be supplied to the outer housing 22 by the tube 82. As shown in FIG. 4, the connecting member 32 of the outer housing 22 can include a removable fiber securing portion 110 that secures the plurality of optic fibers 78 and the light supply fiber 74 in a desired arrangement. The fiber securing portion 110 of the connecting member 32 can be removed from the remainder of the connecting member 32 and modified or replaced so as to provide a different desired arrangement of the plurality of optic fibers 78 and the light supply fiber 74.

Figure 5:
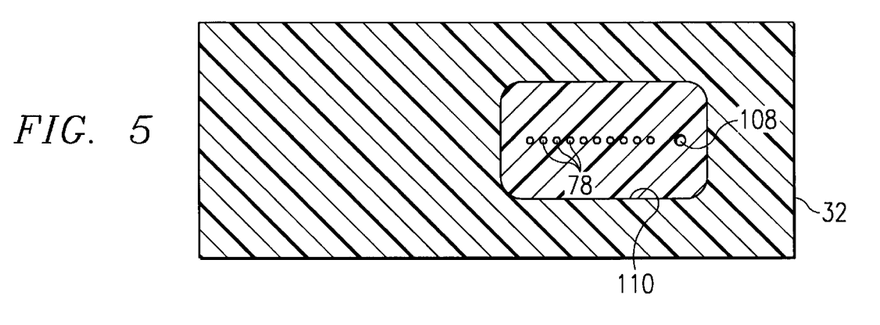
FIG. 5 depicts a cross sectional view of a portion of the apparatus depicted in FIG. 4, taken along the line 5—5 in FIG. 4.

FIG. 5 depicts a cross sectional view of the connecting member 32 of the outer housing 22 depicted in FIG. 4 taken along the line 5—5 in FIG. 4. FIG. 5 depicts the removable fiber securing portion 110 that forms a removable portion of the connecting member. As previously indicated, the removable fiber securing portion 110 provides for the desired arrangement of the plurality of optic fibers 78 and the light supply fiber 74 which can extend through the opening 108.

Figure 6:
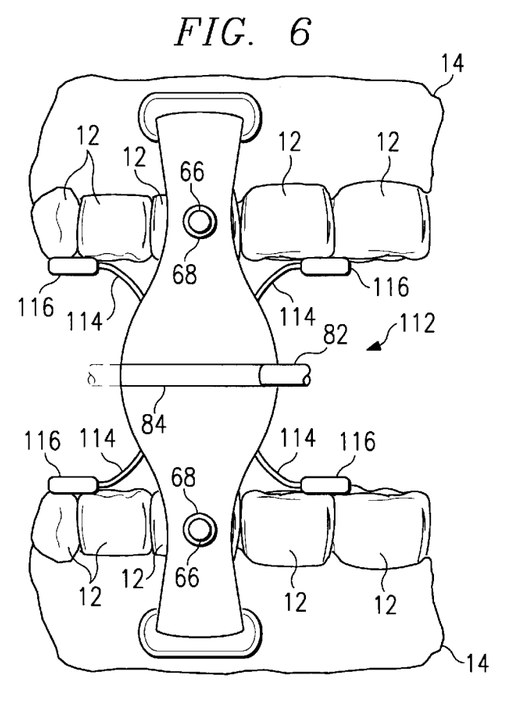
FIG. 6 depicts an elevational view of an apparatus in accordance with the present invention positioned with respect to upper and lower rows of teeth.

FIG. 6 depicts an elevational view of an apparatus 112 in accordance with the present invention. The apparatus 112 can measure the mobility of a first object 12 (a lower tooth) and a second object 12 (an upper tooth). The apparatus 112 is generally the combination of a first apparatus in accordance with FIG. 1 and a second apparatus in accordance with FIG. 1 wherein the second apparatus is generally a mirror image of the first. As shown in FIG. 6, the apparatus 112 is positioned with respect to upper and lower rows of teeth.

To provide further stability to the apparatus 112, a plurality of stabilizing members 114 can be secured to the apparatus 112. The stabilizing members 114 can position a plurality of additional object contact members 116 with respect to adjacent objects 12.

Figure 7:
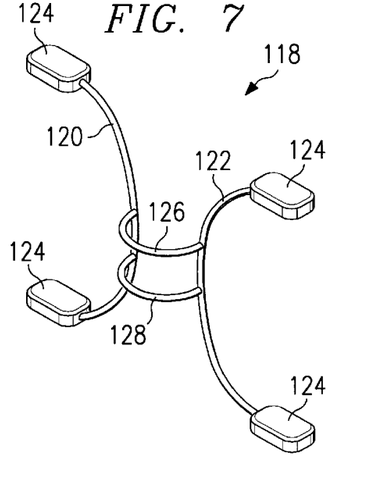
FIG. 7 depicts an apparatus that is releasably attachable to an apparatus in accordance with the present invention to provide additional stability thereto.

FIG. 7 depicts an apparatus 118 that is releasably attachable to the apparatus 112 depicted in FIG. 6 as an alternative to having the stabilizing members 114 secured thereto. Thus, the apparatus 118 includes a stabilizing member 120 and a stabilizing member 122. The stabilizing members 120 and 122 position a plurality of additional object contact members 124. The stabilizing members 120 and 122 are connected to each other by connecting members 126 and 128. The design of the connecting members 126 and 128 allows the apparatus 118 to be releasably attached to the apparatus 112 depicted in FIG. 6 so as to provide further stability to the apparatus 112. The apparatus 118 depicted in FIG. 7 can also be releasably attached to the apparatus 10 depicted in FIG. 1 to provide further stability to the apparatus 10.

A method for measuring the mobility of the object 12 utilizing the apparatus 10 includes the steps of: positioning the apparatus 10 about the object 12; abutting the object contact members 60 and 64 against the object 12; pressing the force transmitting member 66 so as to cause the object contact member 64 to exert a force onto the object 12 which would tend to move the object 12 in a direction radial to the longitudinal axis 16 of the object 12; and, calculating the mobility of the object with respect to the securing medium 14.

As shown in FIG. 1, the object 12 is a tooth and the securing medium 14 is the attached gingiva and alveolar bone of a tooth. Preferably, where the object 12 is a tooth, the side 18 generally faces the facial side of a patient's oral cavity and the side 20 generally faces the lingual (tongue and palatal) side of a patient's oral cavity. Thus, as shown in FIG. 1, an embodiment of the apparatus 10 can be used to measure the mobility of a tooth 12, a portion of which is within and at least loosely secured by attached gingiva and alveolar bone 14. In this embodiment, the object contact members 60 and 64 are dental pads and the securing medium contact members 48 and 50 are gingival pads. The gingival pads 48 and 50 can be any material that is non-irritating to gums under a mild amount of force, such as rubber or organic, synthetic thermoplastic material.

The apparatus 118 depicted in FIG. 7 can be releasably attached to either the apparatus 10 depicted in FIG. 1 or the apparatus 112 depicted in FIG. 6 so as to allow a patient to lightly bite down on the dental pads so as to allow a patient to relax during measurements taken with and to afford further stability to either apparatus.

A method for measuring the mobility of the tooth 12 utilizing the apparatus 10 includes the steps of: positioning the apparatus 10 about the tooth 12; abutting the dental pads 60 and 64 against the tooth 12; pressing the force transmitting member 66 so as to cause the dental pad 64 to exert a force onto the tooth 12 which tends to move the tooth 12 in a direction radial to the longitudinal axis 16 of the tooth 12; and, calculating the mobility of the tooth with respect to the attached gingiva and alveolar bone 14.

While the preferred embodiment of the invention has been described above and illustrated by reference to the accompanying drawings, it is to be understood that many changes may be made thereto without departing from the spirit and scope of the invention, as defined by the appended claims.

That which is claimed is:

1. An apparatus for measuring the mobility of an object having a longitudinal axis, a portion of said object being within and at least loosely secured by a securing medium, said apparatus comprising:

an outer housing at least partially defining a cavity, said outer housing having a first cavity wall portion and a second cavity wall portion, said first and second cavity wall portions facing said cavity, whereby said first and second cavity wall portions are adapted to position said outer housing with respect to said securing medium when said object is disposed in said cavity, said first inner cavity wall portion having an opening therethrough;

an inner housing disposed within said cavity and at least partially defining a chamber capable of receiving said object, said inner housing having a first chamber wall portion facing said chamber and a second chamber wall portion facing said chamber, said first and second chamber wall portions extending generally parallel to the longitudinal axis of said object when said object is disposed within said chamber, said inner housing being adapted for relative movement with respect to said outer housing along a radius to said longitudinal axis;

first and second object contact members for contacting opposing surfaces of said object;

a first compression spring positioned between and in contact with said first chamber wall portion and said first object contact member, a second compression spring positioned between and in contact with said second chamber wall portion and said second object contact member, whereby said first and second object contact members engage opposing sides of said object when said object is disposed within said chamber;

a force transmitting member extending through said opening in said first cavity wall portion so that when said force transmitting member is pressed, said inner housing is moved relative to said outer housing in a direction that is generally radial to the longitudinal axis of said object;

a directional light source for emitting a beam of light, said light source being fixed to one of said object contact members; and a plurality of optic fibers being fixed to said outer housing so as to receive a beam of light emitted from said directional light source; said plurality of optic fibers being in communication with a detector for ascertaining which of said optic fibers receive light emitted from said light source when said apparatus is disposed about said object, said force transmitting member is pressed and said object moves in a direction that is generally radial to the longitudinal axis of said object, said detector providing an output indicative of the amount of mobility of said object with respect to said securing medium.

2. An apparatus in accordance with claim 1 wherein said directional light source for emitting a beam of light can emit a beam of light in a direction which is generally parallel to said longitudinal axis of said object.

3. The apparatus of claim 1 further comprising:

a connecting member pivotally connecting said first and second cavity wall portions of said outer housing, said first cavity wall portion having an upper portion that extends above said connecting member and a lower portion that extends below said connecting member, said second cavity wall portion having an upper portion that extends above said connecting member and a lower portion that extends below said connecting member, such that a force external to said apparatus can be exerted on said upper portions of said first and second cavity wall portions so as to cause said first and second cavity wall portions to pivot with respect to said connecting member so as to allow for the removal of said lower portions of said first and second cavity wall portions from said securing medium.

4. An apparatus in accordance with claim 3 further comprising:

said first chamber wall portion of said inner housing further comprising an opening therethrough;

said second chamber wall portion of said inner housing further comprising an opening therethrough;

a first tension line for retracting said first object contact member from said object, said first tension line being positioned between and in contact with said lower portion of said first cavity wall portion of said outer housing and said first object contact member and extending through said opening in said first chamber wall portion of said inner housing;

a second tension line for retracting said second object contact member from said object, said second tension line being positioned between and in contact with said lower portion of said second cavity wall portion of said outer housing and said second object contact member and extending through said opening in said second chamber wall portion of said inner housing; and whereby said first and second tension lines retract said first and second object contact members from said object when said lower portions of said first and second cavity wall portions of said outer housing are moved generally radially outwardly with respect to the longitudinal axis of said object.

5. An apparatus in accordance with claim 1 further comprising:

first and second securing medium contact members for contacting said securing medium, said first securing medium contact member being positioned between and in contact with said first cavity wall portion of said outer housing and said securing medium when said apparatus is positioned about said securing medium, said second securing medium contact member being positioned between and in contact with said second cavity wall portion of said outer housing and said securing medium when said apparatus is positioned about said securing medium.

6. An apparatus in accordance with claim 1 further comprising a light supply fiber connected to said directional light source for supplying light to said directional light source.

7. An apparatus in accordance with claim 1 wherein said first compression spring and said second compression spring have at least about the same spring force constant.

8. An apparatus in accordance with claim 1 further comprising a first rigid member secured to said first cavity wall portion of said outer housing and a second rigid member secured to said second cavity wall portion of said outer housing.

9. An apparatus in accordance with claim 1 wherein said detector is a digital micrometer.

10. An apparatus in accordance with claim 1 wherein said opening in said second cavity wall portion is threaded, said apparatus further comprising a threaded member that adjustably mates with said threaded opening in said second cavity wall portion so as to allow for the adjustment of the amount that said force transmitting member can be pressed.

11. An apparatus in accordance with claim 1 further comprising a rotatable member rotatably coupled to said outer housing, said rotatable member having an opening therethrough through which extend said plurality of said optic fibers.

12. An apparatus in accordance with claim 11 further comprising a tube fixed to said rotatable member so that said plurality of said optic fibers extend through said opening of said rotatable member and through said tube.

13. A device for measuring the mobility of a first object and a second object comprising a first apparatus in accordance with claim 1 and a second apparatus in accordance with claim 1, said outer housing of said first apparatus being connected to said outer housing of said second apparatus by a rotatable member, whereby said first apparatus can measure the mobility of said first object and said second apparatus can measure the mobility of said second object.

14. An apparatus for measuring the mobility of a tooth having a longitudinal axis, a portion of said tooth being within and at least loosely secured by attached gingiva and alveolar bone, said apparatus comprising:

an outer housing at least partially defining a cavity, said outer housing having a first cavity wall portion and a second cavity wall portion, said first and second cavity wall portions facing said cavity, whereby said first and second cavity wall portions are adapted to position said outer housing with respect to said attached gingiva and alveolar bone when said tooth is disposed in said cavity, said first inner cavity wall portion having an opening therethrough;

an inner housing disposed within said cavity and at least partially defining a chamber capable of receiving said tooth, said inner housing having a first chamber wall portion facing said chamber and a second chamber wall portion facing said chamber, said first and second chamber wall portions extending generally parallel to the longitudinal axis of said tooth when said tooth is disposed within said chamber, said inner housing being adapted for relative movement with respect to said outer housing along a radius to said longitudinal axis;

first and second tooth contact members for contacting opposing surfaces of said tooth;

a first compression spring positioned between and in contact with said first chamber wall portion and said first tooth contact member, a second compression spring positioned between and in contact with said second chamber wall portion and said second tooth contact member, whereby said first and second tooth contact members engage opposing sides of said tooth when said tooth is disposed within said chamber;

a force transmitting member extending through said opening in said first cavity wall portion so that when said force transmitting member is pressed, said inner housing is moved relative to said outer housing in a direction that is generally radial to the longitudinal axis of said tooth;

a directional light source for emitting a beam of light, said light source being fixed to one of said tooth contact members; and a plurality of optic fibers being fixed to said outer housing so as to receive a beam of light emitted from said directional light source; said plurality of optic fibers being in communication with a detector for ascertaining which of said optic fibers receive light emitted from said light source when said apparatus is disposed about said tooth, said force transmitting member is pressed and said tooth moves in a direction that is generally radial to the longitudinal axis of said tooth, said detector providing an output indicative of the amount of mobility of said tooth with respect to said attached gingiva and alveolar bone.

15. An apparatus in accordance with claim 14 further comprising:

a first and second attached gingiva contact member for contacting said attached gingiva, said first attached gingiva contact member being positioned between and in contact with said first cavity wall portion of said outer housing and said attached gingiva when said apparatus is positioned about said attached gingiva and alveolar bone, said second attached gingiva contact member being positioned between and in contact with said second cavity wall portion of said outer housing and said attached gingiva when said apparatus is positioned about said attached gingiva and alveolar bone.

16. An apparatus in accordance with claim 14 wherein said first cavity wall portion of said outer housing is disposed on the facial side of said tooth and said second cavity wall portion of said outer housing is disposed on the lingual side of said tooth.

17. An apparatus comprising a first apparatus in accordance with claim 14 and a second apparatus in accordance with claim 14 wherein said first apparatus is connected to said second apparatus such that said first apparatus can measure the mobility of a first test tooth and said second apparatus can measure the mobility of a second test tooth.

18. An apparatus in accordance with claim 17 wherein said first apparatus and said second apparatus are connected by a rotatable member.

19. A method for measuring the mobility of an object having a longitudinal axis and a portion of which is within and at least loosely secured a securing medium, said method comprising the steps of:

positioning an apparatus, having a first housing and a second housing moveably fixed therein, over and at least partially about said object;

abutting an object contact member against said object, said object contact member being positioned within said second housing;

advancing a force transmitting member, said force transmitting member being capable of contacting said second housing, so as to cause said object contact member to exert a force onto said object tending to move said object in a direction radial to said longitudinal axis of said object; and calculating the mobility of said object with respect to said securing medium from the movement of said object relative to said first housing.

20. A method for measuring the mobility of a tooth having a longitudinal axis and a portion of which is within and at least loosely secured by attached gingiva and alveolar bone, said method comprising the steps of:

positioning an apparatus, having a first housing and a second housing moveably fixed therein, over and at least partially about said tooth;

abutting a tooth contact member against said object, said tooth contact member being positioned within said second housing;

advancing a force transmitting member, said force transmitting member being capable of contacting said second housing, so as to cause said tooth contact member to exert a force onto said tooth;

moving said tooth in a direction radial to said longitudinal axis of said tooth; and calculating the mobility of said tooth with respect to said gingiva and alveolar bone from the movement of said tooth relative to said first housing.

21. An apparatus for measuring the mobility of a tooth having a longitudinal axis, a portion of said tooth being within and at least loosely by attached gingiva and alveolar bone, said apparatus comprising:

a first housing to at least partially encompass said tooth;

a second housing to at least partially encompass and communicate an applied force to said tooth, wherein said second housing is movably fixed within said first housing and adapted to move relative to said first housing;

a force transmitting member contacting said second housing, wherein a force applied to said force transmitting member is communicated to said second housing, initiating movement of said second housing relative to said first housing, and to said tooth; and movement detection means having a fixed portion fixed relative to said first housing and a movable portion which moves in accordance with a movement of said tooth due to said applied force, wherein said movement detection means generates a signal based upon a detected movement of said tooth relative to said fixed portion.

* * * * *